United States Patent
Scarborough et al.

[11] Patent Number: 6,045,580
[45] Date of Patent: Apr. 4, 2000

[54] FUSION IMPLANT DEVICE AND METHOD OF USE

[75] Inventors: Nelson Scarborough, Wayside; John W. Morris, Beachwood, both of N.J.

[73] Assignee: Osteotech, Inc., Eatontown, N.J.

[21] Appl. No.: 09/169,209

[22] Filed: Oct. 9, 1998

Related U.S. Application Data

[62] Division of application No. 08/709,266, Sep. 6, 1996, Pat. No. 5,895,426.

[51] Int. Cl.[7] .................................................. A61F 2/44
[52] U.S. Cl. ............................................... 623/17; 606/61
[58] Field of Search .............................. 623/16, 17, 18; 606/61

[56] References Cited

U.S. PATENT DOCUMENTS

| | | |
|---|---|---|
| 3,703,006 | 11/1972 | Bokros et al. . |
| 3,848,601 | 11/1974 | Ma et al. . |
| 4,059,115 | 11/1977 | Jumashev et al. . |
| 4,185,383 | 1/1980 | Heimke et al. . |
| 4,349,921 | 9/1982 | Kuntz .......................................... 623/17 |
| 4,743,256 | 5/1988 | Brantigan . |
| 4,772,287 | 9/1988 | Ray et al. . |
| 4,820,305 | 4/1989 | Harms et al. . |
| 4,834,757 | 5/1989 | Brantigan . |
| 4,877,020 | 10/1989 | Vich . |
| 4,878,915 | 11/1989 | Brantigan . |
| 4,917,704 | 4/1990 | Frey et al. ................................. 623/17 |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,062,845 | 11/1991 | Kuslich et al. . |
| 5,390,683 | 2/1995 | Pisharodi . |
| 5,423,817 | 6/1995 | Lin . |
| 5,443,514 | 8/1995 | Steffee ....................................... 623/17 |
| 5,445,639 | 8/1995 | Kuslich et al. . |
| 5,458,638 | 10/1995 | Kuslich et al. . |
| 5,484,437 | 1/1996 | Michelson . |
| 5,489,307 | 2/1996 | Kuslich et al. . |
| 5,505,732 | 4/1996 | Michelson . |
| 5,554,191 | 9/1996 | Lahille et al. . |
| 5,653,761 | 8/1997 | Pisharodi . |
| 5,814,084 | 9/1998 | Grivas et al. .............................. 623/17 |
| 5,824,094 | 10/1998 | Serhan et al. ............................. 623/17 |

FOREIGN PATENT DOCUMENTS

| | | |
|---|---|---|
| 307241 | 3/1989 | European Pat. Off. . |
| 0493698 | 7/1992 | European Pat. Off. . |
| 732093 | 2/1996 | European Pat. Off. . |
| 0732093 | 9/1996 | European Pat. Off. . |
| 734703 | 10/1996 | European Pat. Off. . |
| 2636227 | 3/1990 | France . |
| 4302397 | 7/1993 | Germany . |
| 001771 | 2/1993 | WIPO . |
| 93/01771 | 2/1993 | WIPO ........................................ 623/17 |

*Primary Examiner*—David J. Isabella
*Attorney, Agent, or Firm*—Dilworth & Barrese

[57] ABSTRACT

An intervertebral prosthesis includes a bone graft implant member dimensioned for insertion within an intervertebral space defined between adjacent vertebrae and having at least first and second longitudinal sections with respective first and second cross-sectional dimensions. The first cross-sectional dimension of the first implant section is greater than the second cross-section dimension of the second implant section to define a stepped region having a retaining surface. Consequently, upon insertion of the implant member within a generally correspondingly dimensioned receiving bed formed within the adjacent vertebrae, the retaining surface facilitates securement therewithin by corresponding engagement with surfaces of the receiving bed. a method for fusion of adjacent vertebrae utilizing the prosthesis is also disclosed.

13 Claims, 16 Drawing Sheets

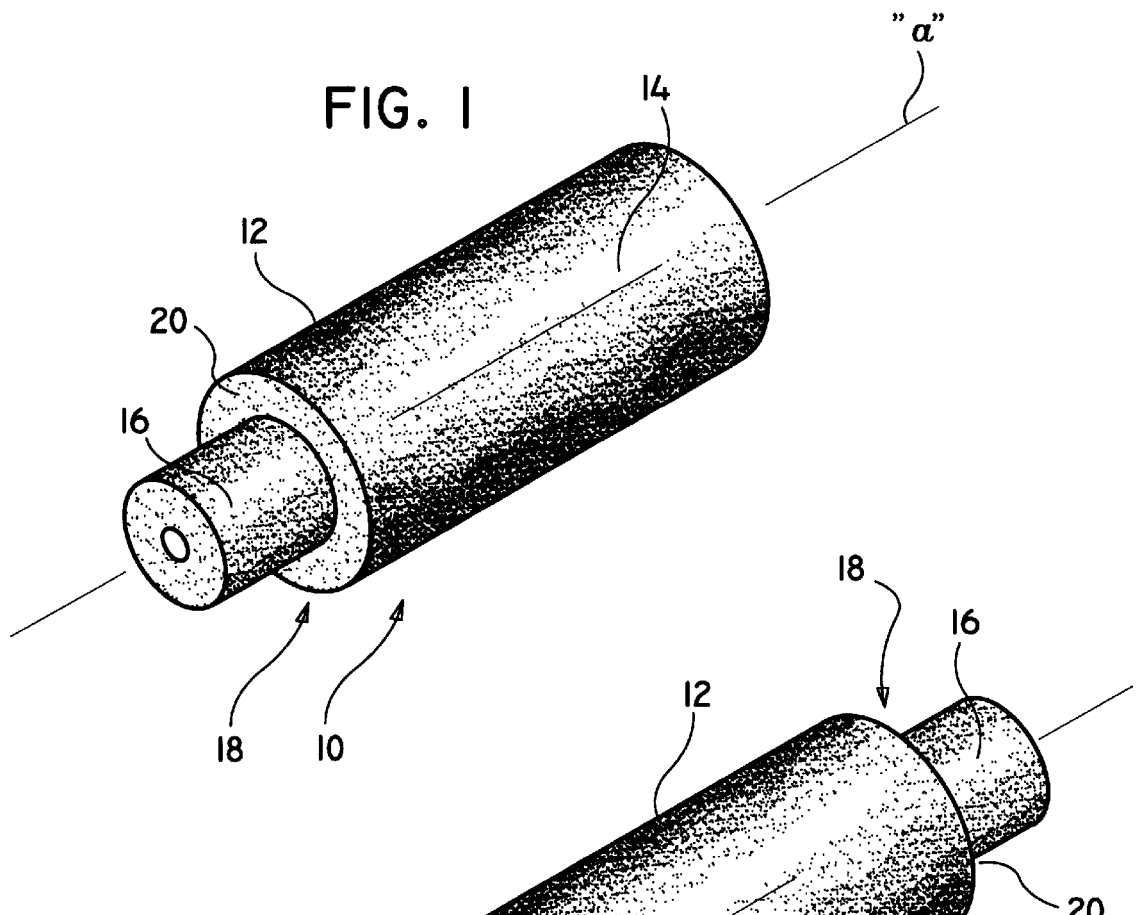

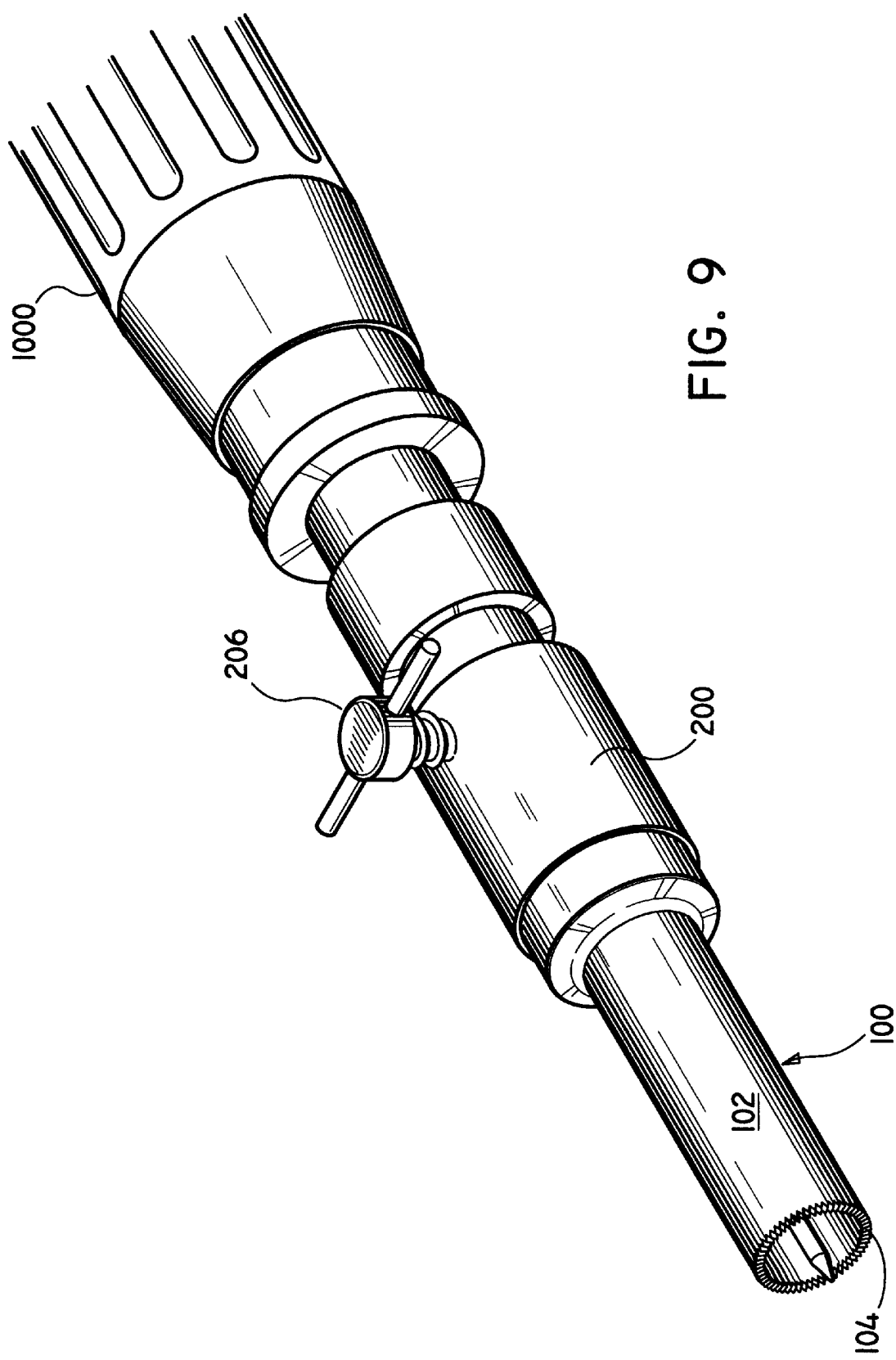

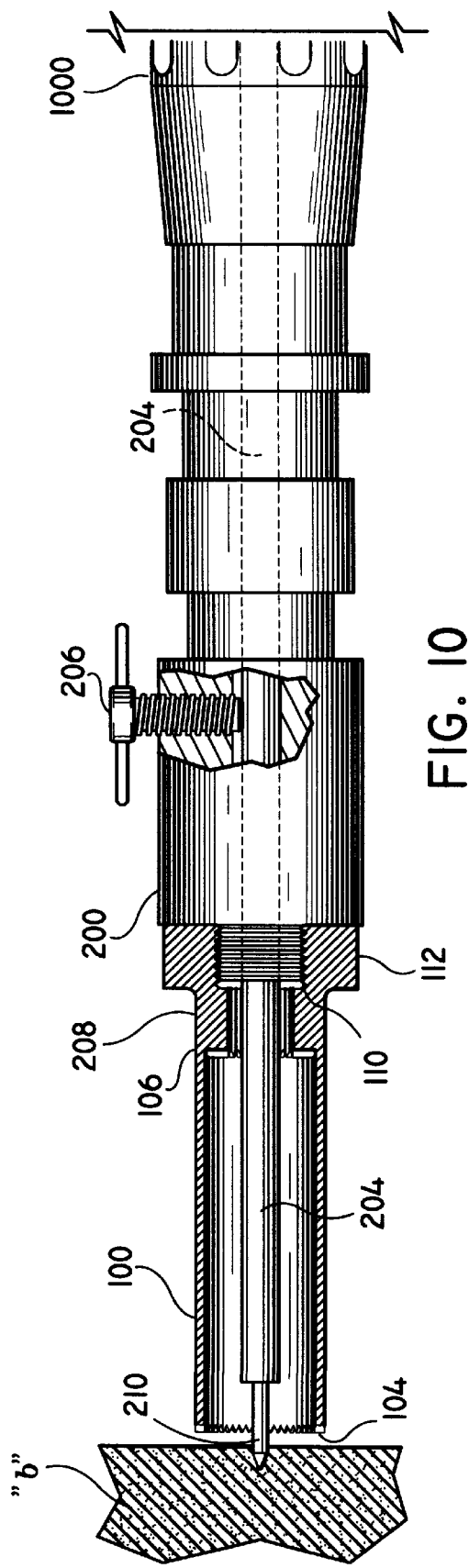
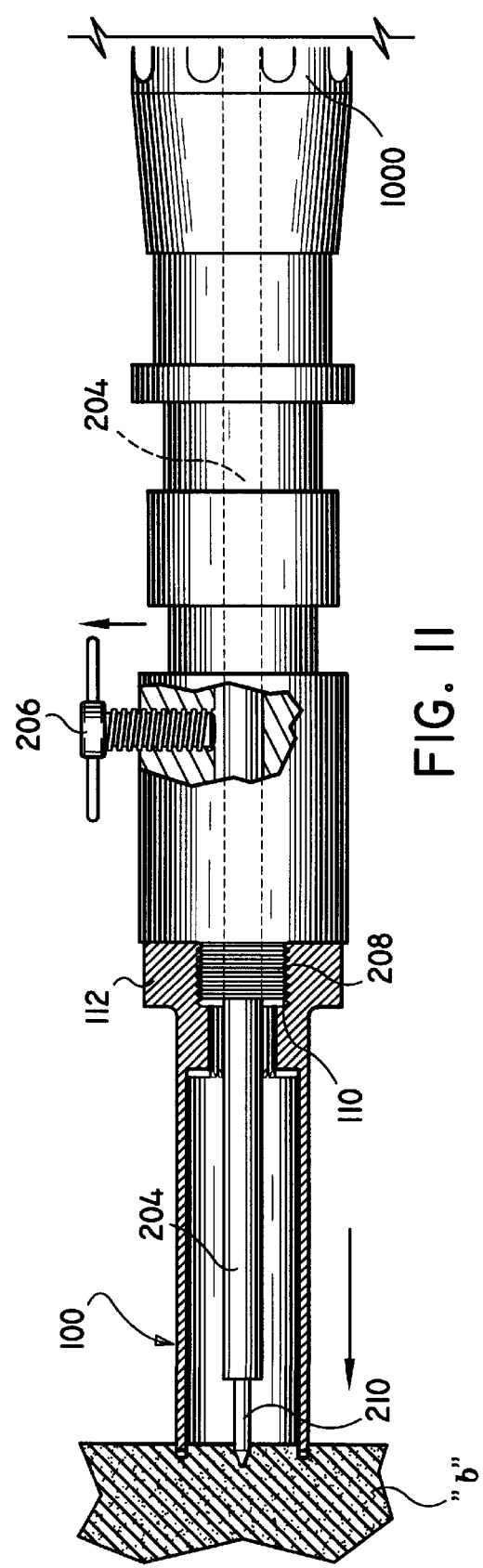

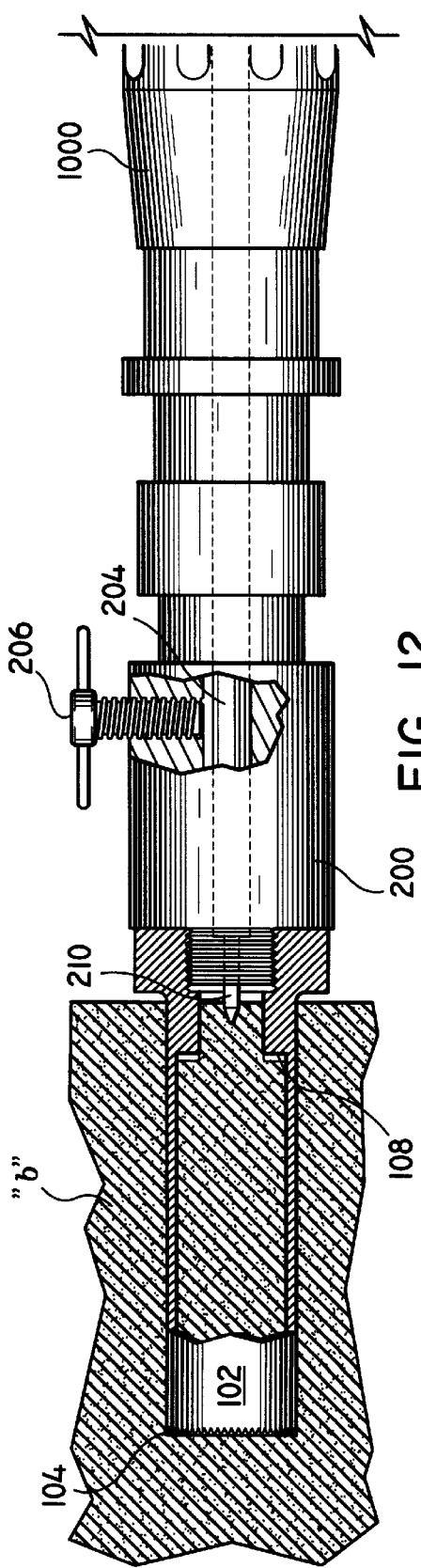
FIG. 12
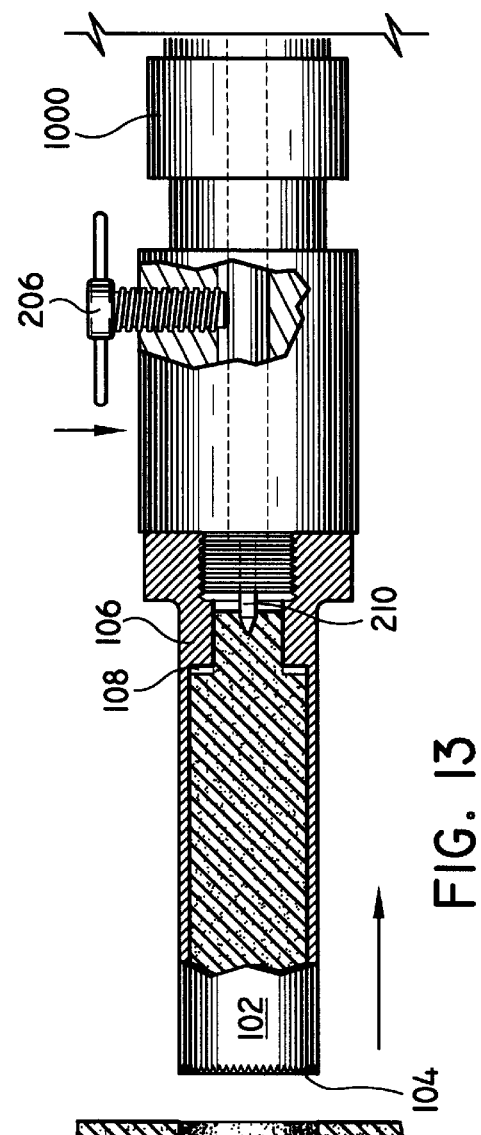
FIG. 13
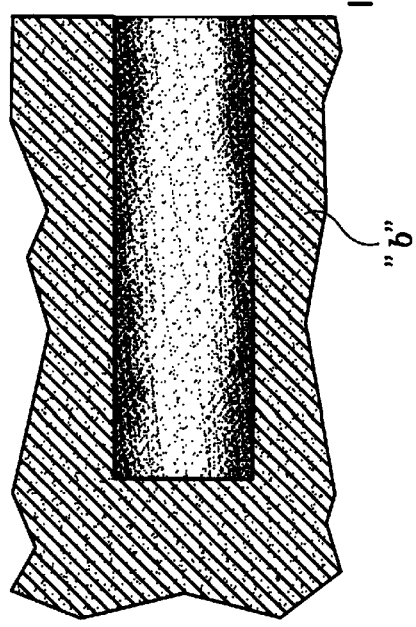

6,045,580

FUSION IMPLANT DEVICE AND METHOD OF USE

RELATED APPLICATION(S)

This application is a divisional of prior application Ser. No. 08/709,266, filed on Sep. 6, 1996, now U.S. Pat. No. 5,895,426.

BACKGROUND OF THE INVENTION

1. Field of the Invention

The present invention relates to an osteogenic interbody fusion implant device and, more particularly, to a non-threaded intervertebral bone implant having a stepped configuration which facilitates securement of the implant within the intervertebral site.

2. Description of the Related Art

The spine is a flexible column formed of a series of bone called vertebrae. The vertebrae are hollow and piled one upon the other, forming a strong hollow column for support of the cranium and trunk. The hollow core of the spine houses and protects the nerves of the spinal cord. The different vertebrae are connected together by means of articular processes and intervertebral, fibro-cartilagineous spaces.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus, both surgical and non-surgical, have been designed to relieve such back pain.

One method, interbody fusion, involves stretching the spine into a natural position so that nerve root canal sizes are increased and nerve irritation is eliminated or reduced. The space between vertebrae is maintained by fusing the vertebrae in the affected area together at a fixed distance. Numerous prosthetic implants have been suggested to fill the void between vertebrae. For example, U.S. Pat. No. 4,936,848 describes a spherical cage implant made of metal or ceramics which is inserted between adjacent vertebrae. The cage has an interior cavity within which bone fragments are inserted. Such bone fragments may be autogenic and are intended to promote subsequent bone growth and fusion of the vertebrae.

Another method of preventing contact of vertebrae is described in U.S. Pat. No. 5,011,484 wherein a stud-shaped insert is inserted longitudinally between two vertebrae and held there by a retainer. U.S. Pat. No. 4,309,777 describes an artificial intervertebral disc having upper and lower discs which are connected to each other by springs. The artificial disc is held in between vertebrae by spikes which project from the disc into the vertebrae. U.S. Pat. No. 4,743,256 describes a rigid, porous plug which can be inserted between vertebrae and held in place by prongs or screws. The porous nature of the plug is alleged to facilitate ingrowth of bone tissue.

An implant bone plug for insertion between vertebrae is also described in U.S. Pat. No. 4,878,915 wherein, in one embodiment, the exterior of the plug is provided with external threading which will, when the plug is rotated, advance the plug into prepared sites between the vertebrae. A portion of the plug is provided with a slot designed to receive the end of a key which is used to rotate the plug. U.S. Pat. No. 5,105,255 describes a method for forming a bore between two adjacent vertebrae and insertion of graft medium such as finely chopped cortical or cancellous bone chips. U.S. Pat. No. 4,961,740 is directed to a substantially open fusion cage which is inserted between adjacent bony surfaces between vertebrae by screwing the cage into place. The cage may be filled with bone chips or other bone inducing substances and, when inserted into the intervertebral space, immediate contact between the bone inducing substance contained within the cage and the native bone occurs through the outer surface of the cage.

Ideally, a fusion graft should stabilize the intervertebral space and become fused to adjacent vertebrae. Moreover, during the time it takes for fusion to occur, the graft should have enough structural integrity to withstand the stress of maintaining the space without substantially degrading or deforming and have sufficient stability to remain securely in place prior to actual bone ingrowth fusion. Consequently, a fusion graft should contain some kind of anchor and, additionally, a bone inducing substance which causes rapid bone-growth and quick fusion of the graft to adjacent vertebrae. Furthermore, the material from which the fusion graft is made should be biocompatible and closely mimic the body's naturally occurring tissues.

All the above-described implants are intended to support and maintain an appropriate intervertebral space. Unfortunately, those implants may not fit certain ideal criteria for an interbody fusion graft. For example, many of the implants such as the one described in U.S. Pat. No. 4,936,848 are made of metals and ceramics and, while biocompatible, do not precisely mimic the body's natural bone tissue. U.S. Pat. No. 5,015,255 describes a graft in the form of bone chips which may eventually result in fusion between the vertebrae. If adequate fusion of the bone chips occurs, the final fused graft may closely mimic the body's naturally occurring tissues. However, when the bone chips are inserted, they are unconfined and may not remain contained between the vertebrae for a sufficient time to adequately false to each other and to adjacent vertebrae. The bone plug disclosed in U.S. Pat. No. 4,878,915 has a threaded outer surface to assist in placement of the implant between the adjacent vertebrae. The external threads, however, compromise the strength of the implant. In addition, the threaded bone implant may have a tendency of backing out of the prepared bore.

Consequently, there is a need for improved interbody fusion implants which more closely adhere to the ideal of a spinal fusion implant.

SUMMARY

Accordingly, the present invention is directed to an intervertebral prosthesis. The prosthesis includes an implant member (preferably, bone) dimensioned for insertion within an intervertebral space defined between adjacent vertebrae and having at least first and second longitudinal sections with respective first and second cross-sectional dimensions. The first cross-sectional dimension of the first implant section is greater than the second cross-section dimension of the second implant section to define a stepped region having a retaining surface. Consequently, upon insertion of the implant member within a generally correspondingly dimensioned receiving bed formed within the adjacent vertebrae, the retaining surface facilitates securement therewithin by corresponding engagement with surfaces of the receiving bed.

The implant member is preferably generally circular in cross-section with the second longitudinal section defining a diameter ranging from about 50% to about 95% the diameter defined by the first longitudinal section. A single step implant is preferred, however, a multiple stepped implant is also contemplated. The implant member may also define an interior hollow cavity for accommodating bone growth inducing material. At least one opening may extend through the outer wall of the implant member to permit communication with bone growth inducing material disposed within the hollow cavity to facilitate the fusion process.

A method for fusion of adjacent vertebrae utilizing the prosthesis is also disclosed.

BRIEF DESCRIPTION OF THE DRAWINGS

Preferred embodiments of the disclosure are described herein with references to the drawings wherein:

FIG. 1 is a frontal perspective view of the stepped bone fusion implant in accordance with the principles of the present disclosure;

FIG. 2 is a rear perspective view of the fusion implant of FIG. 1;

FIG. 9 is a perspective view of the distal end portion of a cutter instrument having the implant cutter of FIGS. 3–5 mounted thereto;

FIG. 10 is a side elevational view of the cutter instrument with the implant cutter in cross-section illustrating positioning of the implant cutter adjacent the bone mass with the drill guide of the instrument penetrating the mass;

FIG. 11 is a view similar to the view of FIG. 10 illustrating the cylindrical cutting blade of the implant cutter penetrating the bone mass;

FIG. 12 is a side elevational view of the cutting instrument with portions of the implant cutter removed illustrating the cylindrical cutting blade fully advanced to form the stepped fusion implant;

FIG. 13 is a view similar to the view of FIG. 12 illustrating removal of the implant cutter with the formed stepped fusion implant from the bone mass;

DETAILED DESCRIPTION OF THE PREFERRED EMBODIMENT(S)

Figure 4:
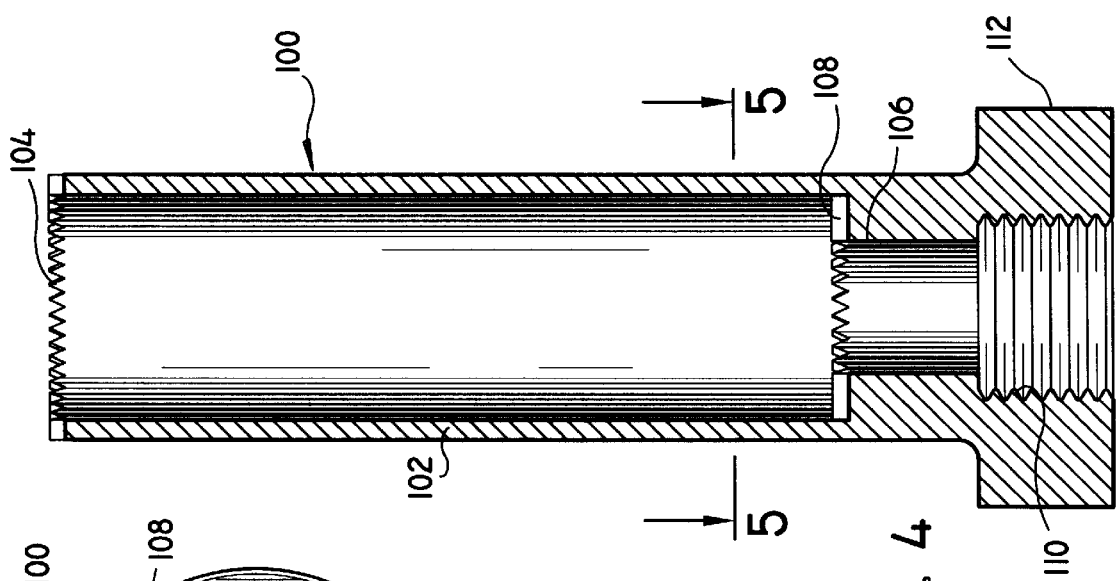
FIG. 4 is a side cross-sectional view of the implant cutter of FIG. 3.

The spinal interbody fusion device according to the present invention is intended to be placed between adjacent vertebrae in an attempt to correct a debilitating degeneration of the spinal structure. In humans, the device may be used predominantly in the lumbar region of the spine, but, is adjustable for use in the thoracic and cervical regions as well. When in place, the device supports and maintains an appropriate distance between vertebrae and causes bone tissue to form and become integral with the device. Consequently, the intervertebral space becomes filled with autologous bone tissue and forms an integral rigid bone connection between adjacent vertebrae.

Referring now to FIGS. 1–2, the fusion implant of the present invention will be described. Implant 10 includes elongated body 12 which is fabricated from cortical and/or cancellous bone. The bone may be autologous, allogenic or xenogeneic and is preferably retrieved from the humerus, tibia, femora, etc . . . as is known in the art. As shown, elongated body 12 defines a longitudinal axis "a" and has first and second longitudinal sections 14, 16 respectively. First and second longitudinal sections 14, 16 are preferably cylindrical in configuration and are concentrically arranged about the longitudinal axis "a".

First longitudinal section 14 has a cross-sectional dimension which is greater than the cross-sectional dimension of second longitudinal section 16 thereby defining a stepped region 18 at the juncture of the two sections 14, 16. As will be appreciated from the description below, stepped region 18 defines a retaining surface 20 which facilitates the retention of fusion implant 10 between adjacent vertebrae, e.g., within a specially prepared bed created within adjacent vertebrae, thereby ensuring that the implant 10 will not dislodge during the healing process. In a preferred embodiment, first longitudinal section 14 has a diameter ranging between about 8 and 20 millimeters (mm), more preferably, between about 12 and 16 millimeters (mm). Second longitudinal section 16 has a diameter which is preferably about 2 min less than the diameter of the first section 14. The length of elongated body 12 ranges from about 10–35 mm, preferably about 15–30 mm.

In a preferred embodiment, second section 16 has a greater density than first section 14. In this manner, the smaller diameter of second section 16 will not compromise the overall strength of the implant 10. The greater density of the second section 16 is achieved during harvesting and formation of the implant. As will be discussed in greater detail hereinbelow, when retrieving the implant from the tibia (i.e., in the case of cancellous plugs), second section 16 is retrieved from the harder and more dense proximal subchondral bone while first section 14 is retrieved from cancellous bone area.

Figure 5:
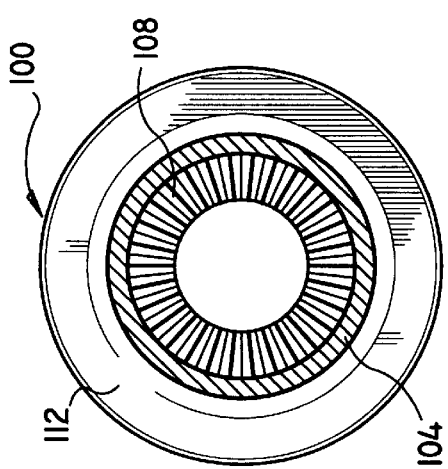
FIG. 5 is a view of the implant cutter taken along the lines 5—5 of FIG. 4.
Figure 3:
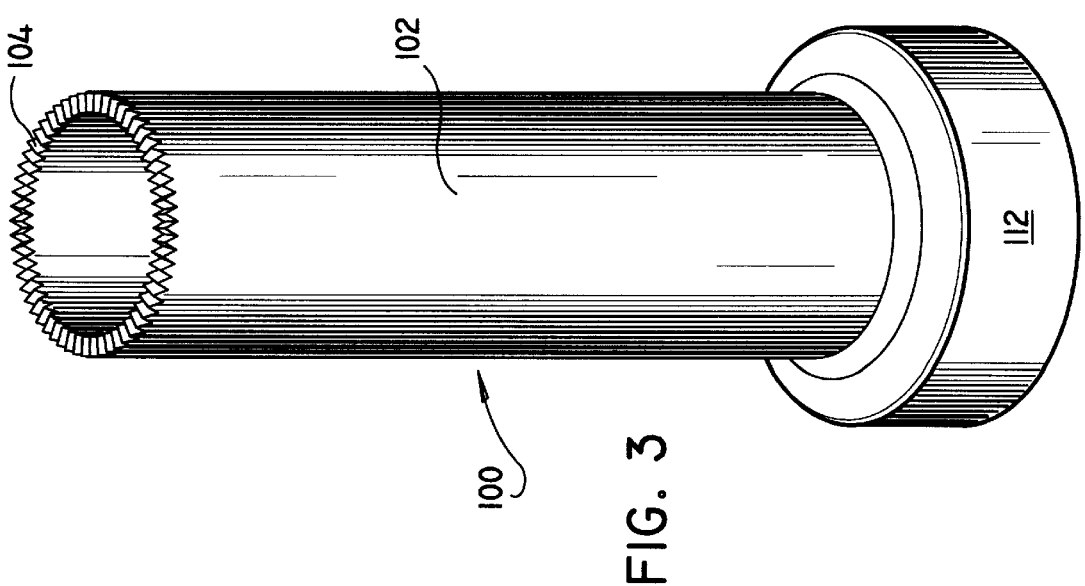
FIG. 3 is a perspective view of a novel implant cutter for forming the bone fusion implant of FIGS. 1–2.

Referring now to FIGS. 3–5, there is illustrated a novel implant cutter for forming the stepped fusion implant 10 of the present invention. Implant cutter 100 is mountable to a conventional rotatable drill instrument as will be discussed. Implant cutter 100 includes outer hollow drill portion 102 with cutting teeth 104 and inner hollow drill portion 106 with Cutting teeth 108. In general, outer drill portion 102 serves in forming first longitudinal section 14 of implant 10 while inner drill portion 106 serves in forming second longitudinal section 16. Inner drill portion 106 is proximally positioned with respect to outer drill portion 102 whereby teeth 108 of inner drill portion extend to the inner wall of outer drill portion 102 as shown in FIGS. 4–5.

As best depicted in FIG. 5, implant cutter 100 includes a proximally disposed internal threaded portion 110 which mates with corresponding structure of a drill instrument to mount the implant cutter 100 to the instrument. Implant cutter 100 further includes a proximal flange 112 to facilitate its handling and mounting to the instrument.

Figure 7:
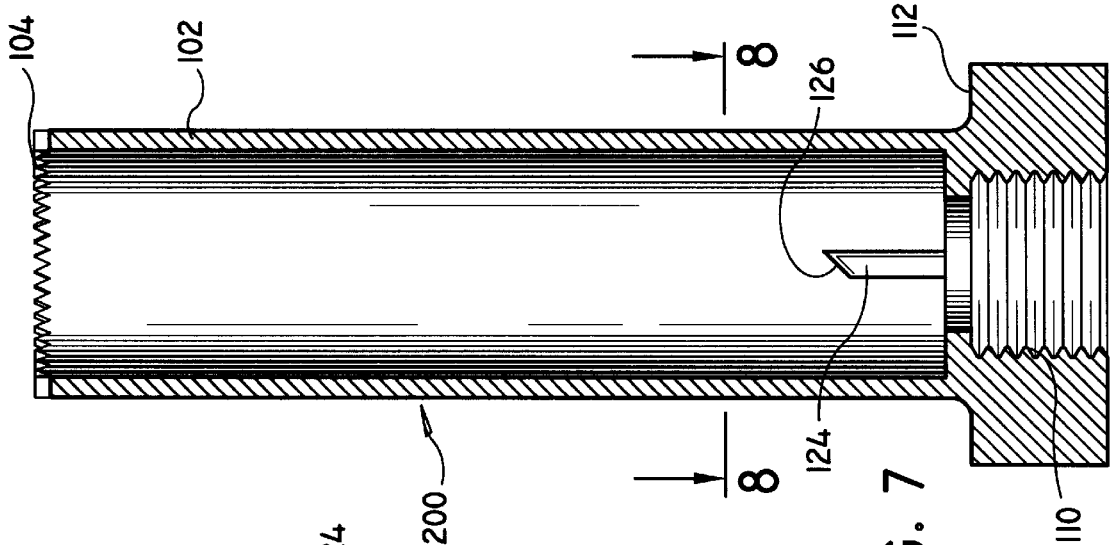
FIG. 7 is a side cross-sectional view of the implant cutter of FIG. 6.
Figure 8:
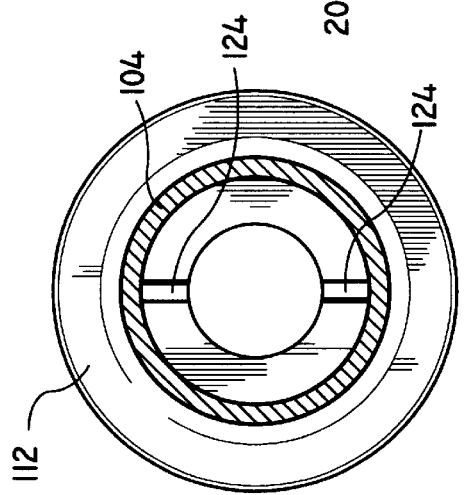
FIG. 8 is an axial view of the implant cutter taken along the lines 8—8 of FIG. 7.
Figure 6:
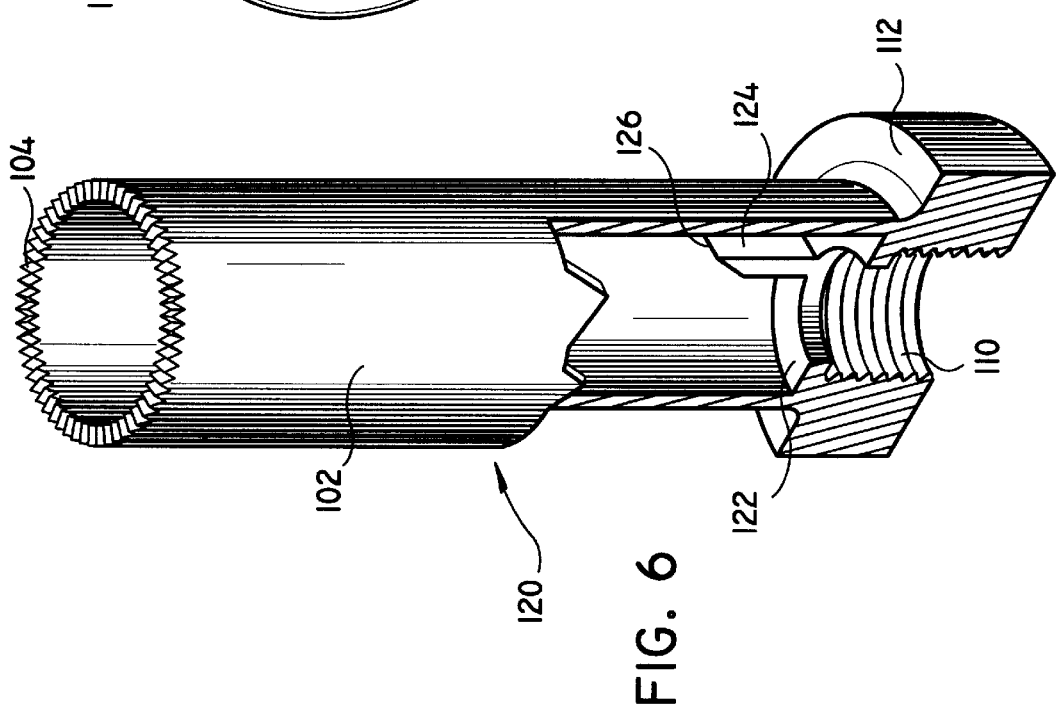
FIG. 6 is a perspective view with portions cult away of an alternative embodiment of the implant cutter of FIG. 3.

FIGS. 6–8 illustrate an alternate embodiment of the implant cutter of FIGS. 3–5. Implant cutter 120 of this embodiment is similar to the implant cutter 100, but, includes an inner drill portion 122 having two diametrically opposed axial teeth 124. Diametrical teeth 124 have transverse cutting edges 126 which cut the bone to form the second longitudinal section 16 of the implant. In all other respects, the implant cutter 200 is identical to the cutter of FIGS. 3–5.

Referring now to FIG. 9, there is illustrated implant cutter 100 of FIGS. 3–5 mounted to the distal end of a conventional cannulated surgical drill instrument 1000. Implant cutter 100 is shown incorporated with a mounting assembly 200 serves in mounting the implant cutter 100 to the drill instrument 1000. This particular mounting assembly contemplated is disclosed in commonly assigned U.S. patent appln. Ser. No. 08/404,255, filed Mar. 15, 1995, the contents of which are incorporated herein by reference. The mounting or Cutting assembly 200 disclosed in the '255 application includes mounting member 202, support shaft 204 (FIG. 10) and threaded fitting 206. Mounting member 202 has a proximal end configured for mounting to a chuck of the drill instrument 1000 and a distal threaded stein 208 which threadably engages internal thread 110 of implant cutter 100 as shown in FIG. 10 to mount the cutter 100. Support shaft 204 traverses an axial bore disposed within mounting member 202 and extends proximally through an associated bore of the instrument (as shown in phantom in FIG. 10) and distally through implant cutter 100. Support shaft 204 has a drill guide 210 mounted to its distal end, which forms a pilot hole to assist in guiding implant cutter 100 into the bone mass. Threaded fitting 206 extends through mounting member 202 and serves in selectively securing support shaft 204 at desired longitudinal positions relative to mounting member 202. Further details of the mounting assembly 200 may be ascertained by reference to the '255 application.

Formation of Bone Implant

The formation of bone implant 10 utilizing implant cutter 100, in conjunction with mounting assembly 200 and cannulated drill instrument 1000, will now be discussed.

Referring now to FIGS. 10–13, there is illustrated, in sequence, a preferred method for forming the bone fusion implant 10 of FIGS. 1–3. With initial reference to FIG. 9, implant cutter 100 is mounted via mounting assembly 200 to drill instrument 1000 as previously described. Referring now to FIG. 10, with threaded fitting 206 of mounting assembly engaged against support shaft 204, drill guide 210 is driven into bone mass "b" to form a pilot hole as depicted. Bone mass "b" may represent the tibia or the iliac crest. The drill instrument 1000 is then actuated to impart rotational movement to implant cutter 100. Implant cutter 100 is advanced into the bone mass "b" such that cutting edge 104 of outer drill portion 102 penetrates bone mass "b". Upon penetration of Cutting edge 104 into the bone mass "b" (as depicted in FIG. 11), the drill instrument 1000 is stopped. Threaded fitting 206 is rotated to a release position (FIG. 11) to liberate support shaft 204 thereby permitting the support shaft 204 to slide proximally as the implant 100 is formed, i.e., as implant cutter 100 is advanced into the bone mass "b".

With reference now to FIG. 12, drill instrument 1000 is once again actuated and advancing movement of implant cutter 100 into bone mass "b" is continued. During such advancing movement, cutting teeth 104 of outer drill portion 102 core or cut the bone mass "b" to form the first longitudinal section 14 of the implant. Further advancing movement of implant cutter 100 results in cutting teeth 108 of inner drill portion 108 to core or cut the bone material received within implant cutter 100 to form the second longitudinal section 16 of the implant. Implant cutter 100 is advanced into bone mass "b" until flange of the implant cutter 100 abuts the bone mass "b". When drilling into the tibia to lowest implant 10, outer dull portion 102 cores the underlying cancellous bone to form the less dense first longitudinal section 14 of the implant while inner dull portion 108 cores the more dense subchondral bone to form the more denser second longitudinal section 16 of the implant 10.

With bone implant 10 fully formed, drill instrument 1000 is stopped. Threaded fitting 206 is once again tightened against support shaft 204, and implant cutter 100 with the formed implant disposed therein is withdrawn from bone mass "b" as depicted in FIG. 13. Bone implant 10 is thereafter removed from implant cutter 100 by releasing fitting thread 206 and advancing Support shaft 204 distally to eject the implant 10 from the implant cutter 100. In some instances, the bone implant may not be removed within implant cutter 100. It would be removed in this case by cutting laterally using a standard oscillating saw blade or other cutting device.

Spinal Fusion Procedure

The insertion of fusion implant in conjunction with a posterior approach for lumbar discectomy and spinal fusion will be discussed. It is to be appreciated that other surgical approaches, e.g., anterior, postero-lateral, etc . . . may be utilized to perform the discectomy and insert implant 100 as well.

Figure 14:
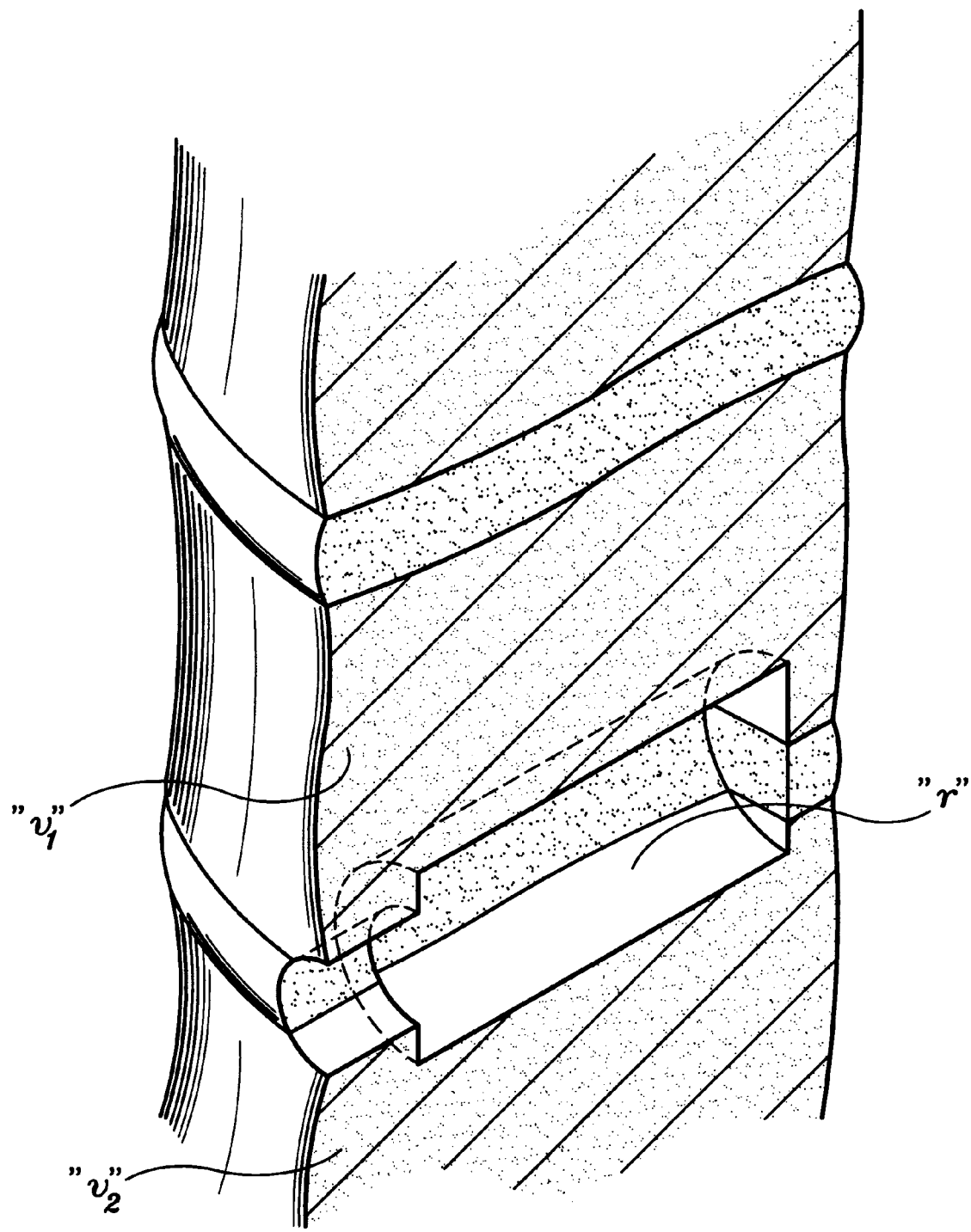
FIG. 14 is a perspective view of a portion of the spinal column illustrating an implant receiving bed formed within adjacent vertebrae for reception of the stepped fusion implant.

Initially, the vertebral column is accessed via a posterior approach with the use of appropriate retractors to retract neighboring muscle tissue, blood vessels and/or nerve tissue. Thereafter, at least a portion of the degenerative disc is removed with an appropriate rongeur or cutting implements. With reference now to FIG. 14, a receiving bed "r" corresponding generally in shape to fusion implant 10 is formed in opposed faces of the adjacent vertebrae $V_1$, $V_2$. The receiving bed "r" may be prepared by drilling or chiseling. Such techniques are well known in the art. The prepared sites are preferably sufficiently dimensioned to span the central soft cancellous bone and include the hard cortical bone of the adjacent vertebrae $V_1$, $V_2$.

Figure 15:
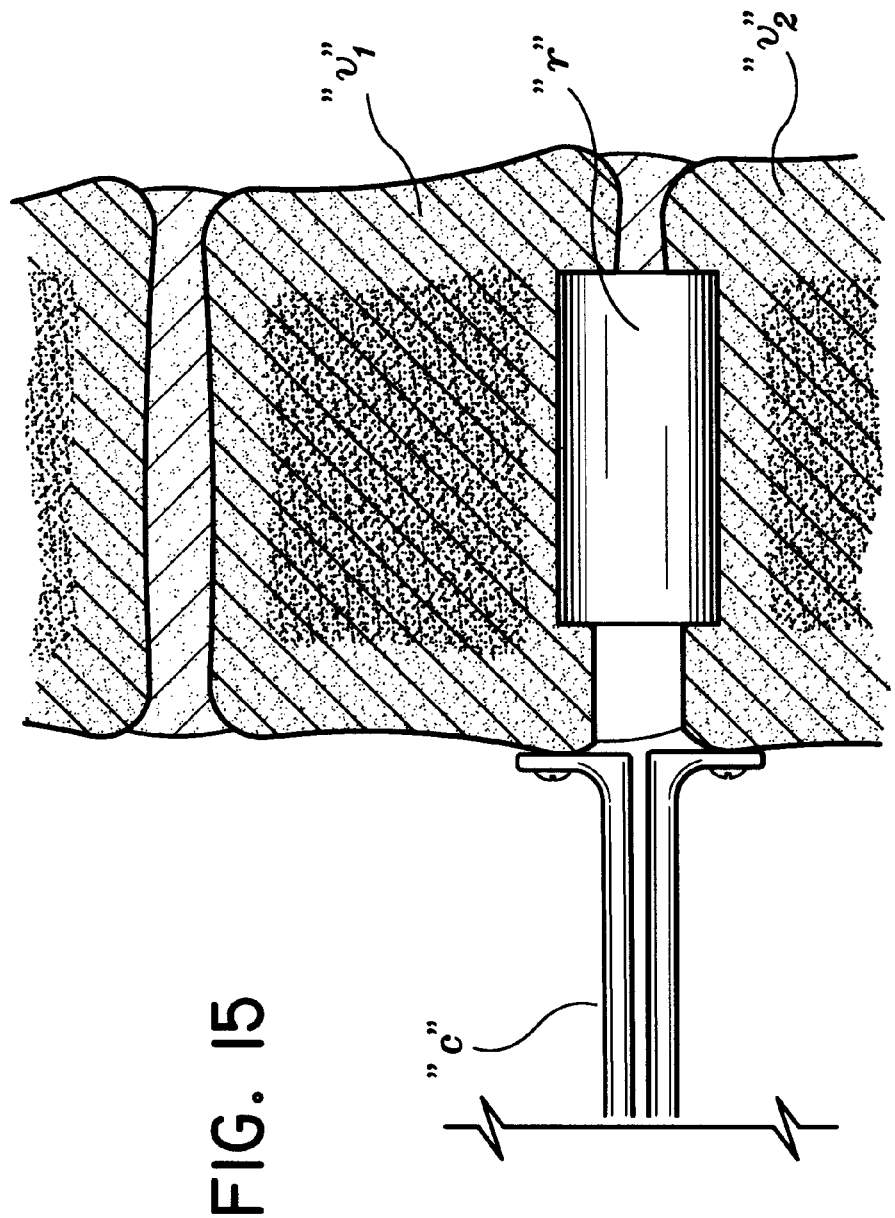
FIG. 15 is a view illustrating a lumbar spreader mounted to adjacent vertebrae to distract the vertebrae to facilitate insertion of the fusion implant.
Figure 16:
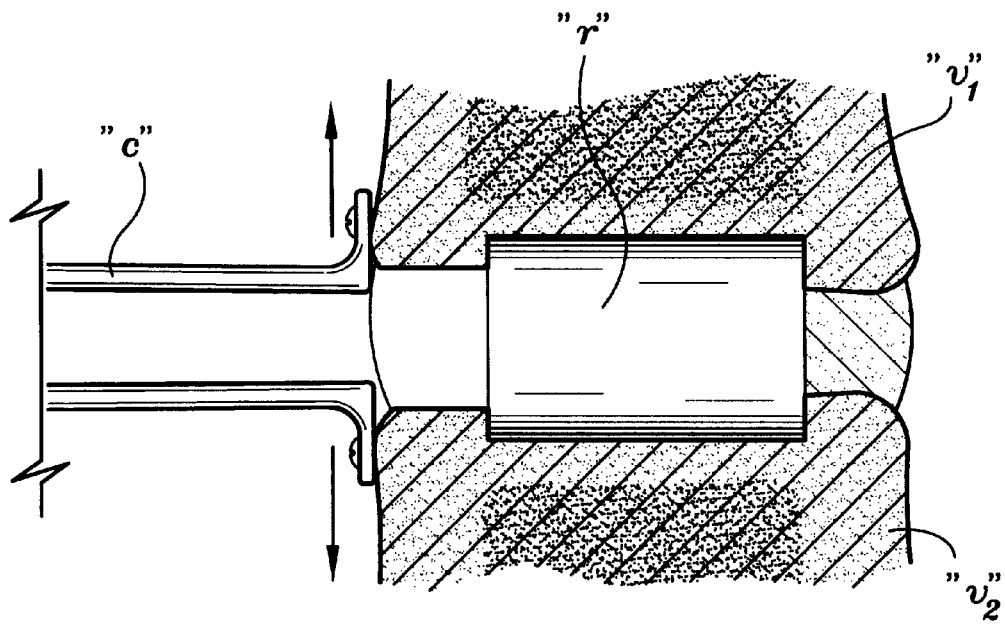
FIG. 16 is a view similar to the view of FIG. 15 illustrating the adjacent vertebrae distracted by the lumbar spreader.
Figure 17:
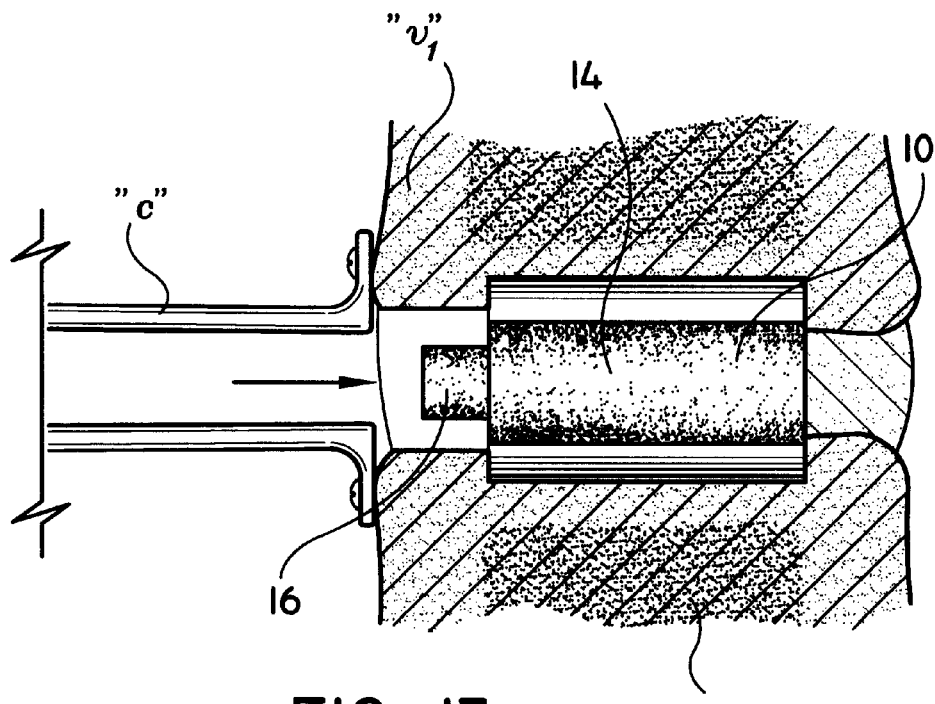
FIG. 17 is a view illustrating insertion of the fusion implant between the distracted vertebrae and within the implant receiving bed.

With reference now to FIG. 15, a retractor "c" is mounted to the posterior faces of the vertebrae $V_1$, $V_2$. One retractor "c" suitable for this purpose is the Cloward Lumbar Lamina Spreader manufactured by Codman. The retractor "c" includes a pair of retractor arms which are mountable to the posterior vertebral faces via screws as is shown. With the retractor "c" appropriately mounted, the arms of the retractor are spread to distract the adjacent vertebrae as depicted in FIG. 16 to provide adequate clearance for insertion of fusion implant 100 within receiving bed "r". Fusion implant 100 is thereafter inserted into the distracted space with an appropriate grasping instrumentation (not shown) where it is received within the receiving bed "r" as shown in FIG. 17. Once fusion implant 10 is appropriately positioned within the receiving bed "r", the retractor "c" is returned to return the adjacent vertebrae $V_1$, $V_2$ to their normal positions.

Figure 19:
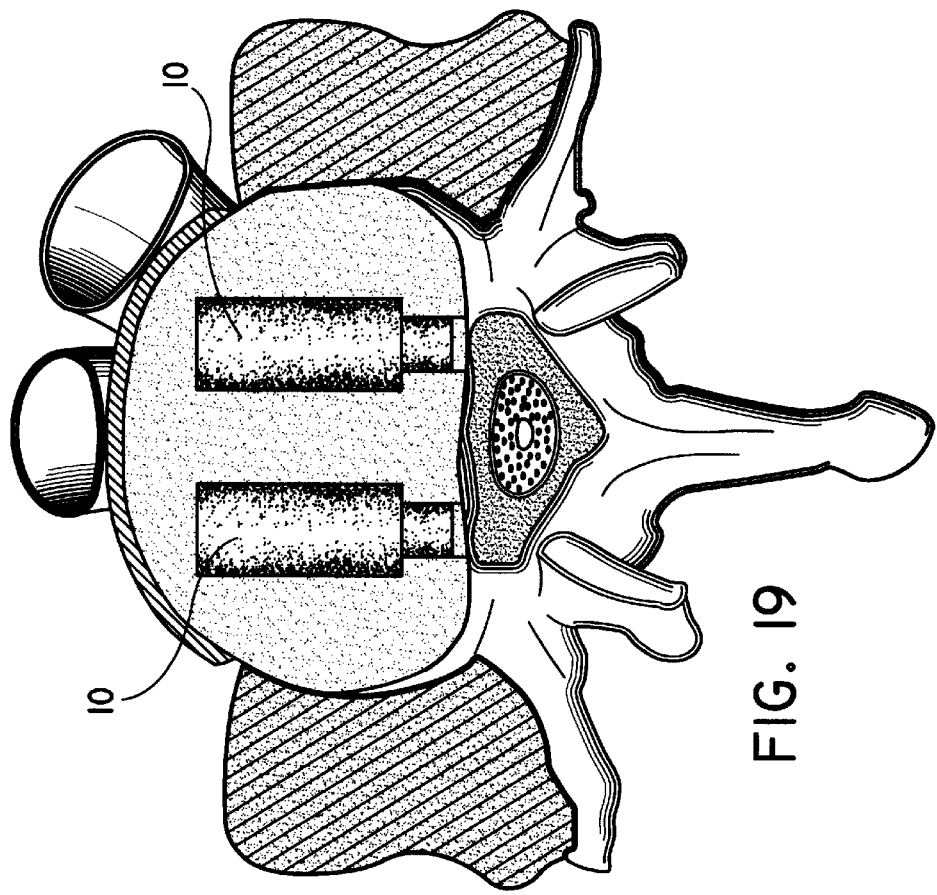
FIG. 19 is a sectional view of the vertebral column illustrating the positioning of a pair of fusion implants in the vertebral column through a posterior approach.
Figure 18:
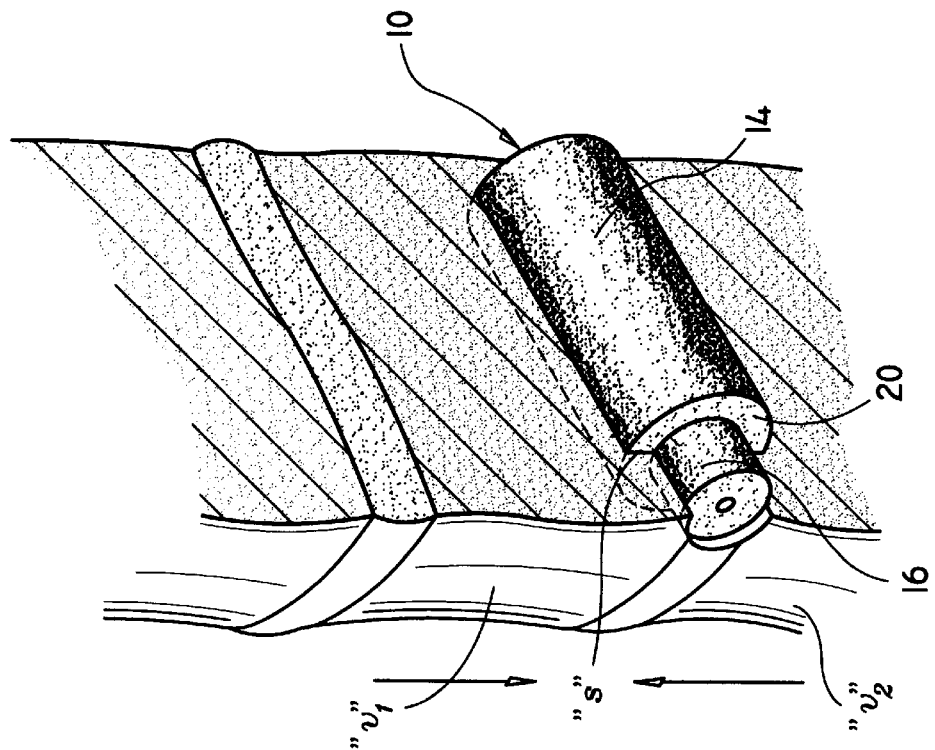
FIG. 18 is a view illustrating the fusion implant received within the implant receiving bed.

As depicted in FIG. 18, the fusion implant 10 forms a strut supporting and maintaining the adjacent vertebrae $V_1$, $V_2$ in desired spaced relation. In practice, optimum dimensions for the fusion implant 100 are determined, in part, by the dimensions of the receiving bed "r" between the adjacent vertebrae. The stepped region 18 defined at the juncture of the first and second longitudinal sections 14, 16 prevents the inserted implant from "backing out" (retropulsing) or becoming dislodged due to the engagement of retaining surface 20 with vertebral surfaces "s" defined by the receiving bed. In this manner, fusion implant 10 is permanently fixed within the intervertebral space. As depicted, the smaller diameter second section 16 of implant 10 allows for inter-position between the vertebral endplates. As indicated above, second implant section 16 is relatively dense thereby providing the appropriate rigidity to support the vertebrae. Over a period of time, the adjacent vertebral bodies grow within and fuse with implant 10 to form a solid fusion. FIG. 19 illustrates two fusion implants 10 positioned with in the intervertebral space.

Figure 19A:
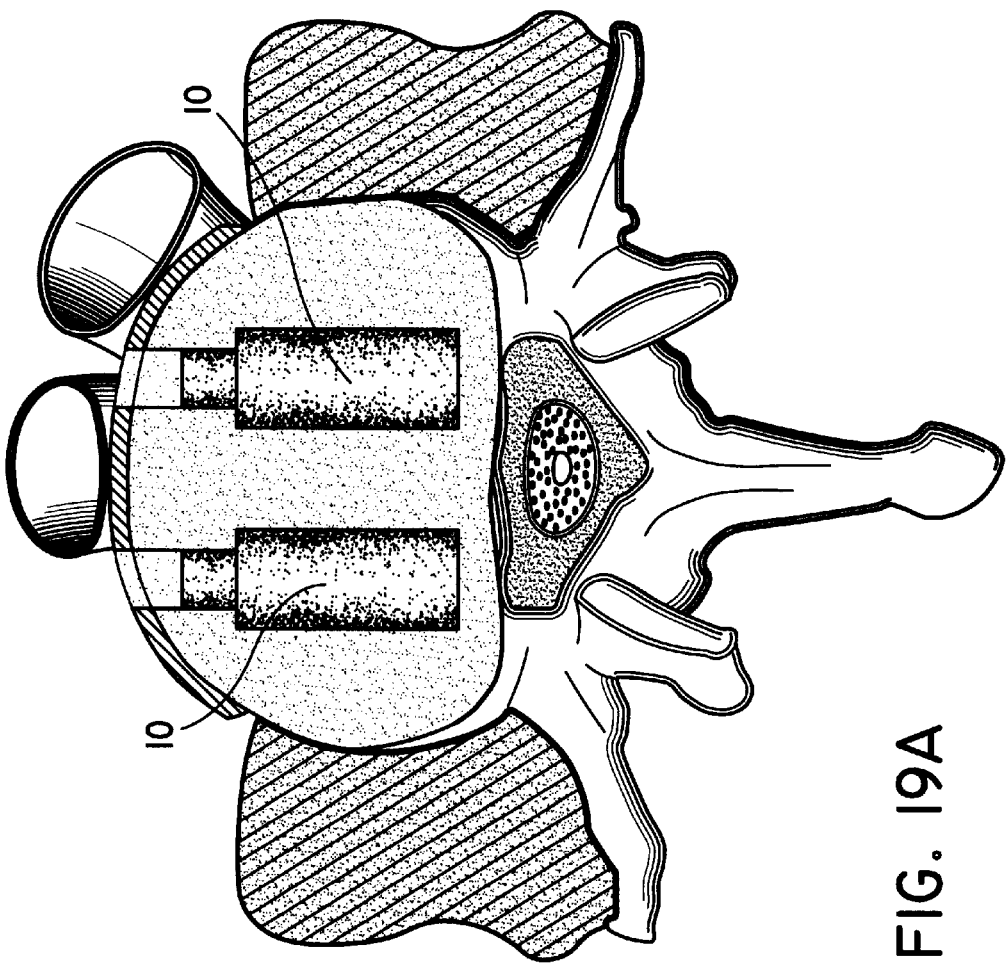
FIG. 19A is a sectional view of the vertebral column illustrating the positioning of a pair of fusion implants in the vertebral column through all anterior approach.

FIG. 19A illustrates two fusion implants 10 positioned within the intervertebral space through a conventional anterior approach. It is to be appreciated that an anterior approach may be readily utilized to position the implants 10.

Alternate Embodiments

Figure 21:
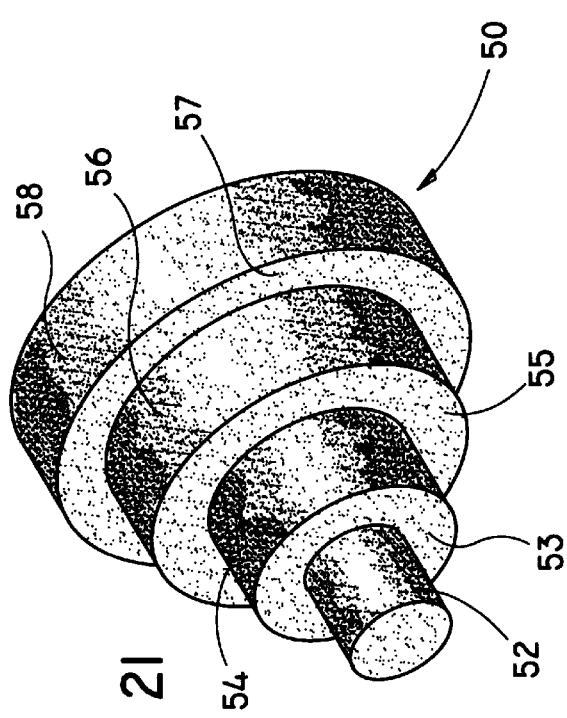
FIGS. 20–25 are perspective view of alternate embodiments of the fusion implant of FIGS. 1–2.
Figure 20:
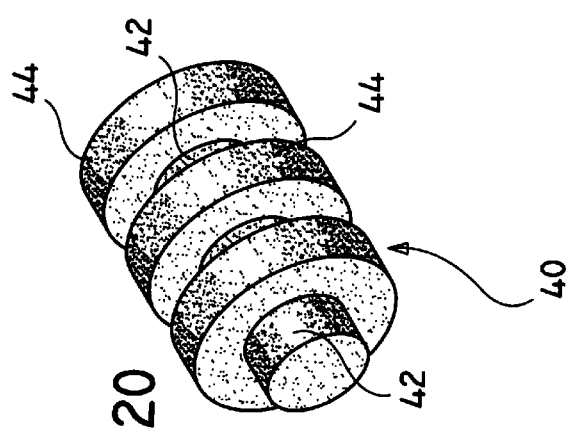
Figure 22:
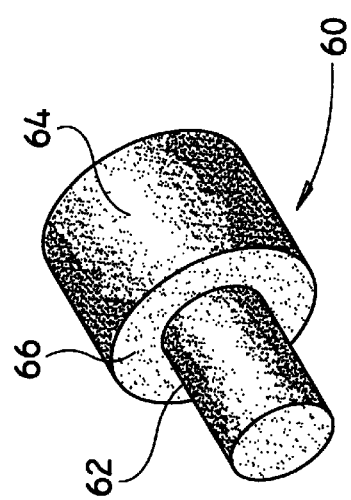

FIGS. 20–25 illustrate alternate embodiments of the stepped fusion implant of the present invention. Fusion implant 40 of FIG. 20 is a multi-step configuration defined by a plurality of alternating sections 42, 44 of different cross-sectional dimensions. In particular, implant section 42 has a first diameter which is less than the diameter of second implant section 44. The junctures of the first and second implant sections 42,44 define stepped regions with retaining surfaces 46 which engage corresponding structure defined by the receiving bed within the adjacent vertebrae. FIG. 21 illustrates another multi-step implant 50 where the implant sections 52,54, 56,58 sequentially increase in cross-sectional dimension from one end of the implant to the other end to define a multitude of retaining surfaces 53,55,57. FIG. 22 depicts a single step fusion implant 60 similar to the implant of FIGS. 1–3. However, in accordance with this embodiment, it is contemplated that the smaller implant section 62 will be the leading end, i.e., during insertion within the adjacent vertebrae $V_1$, $V_2$ the smaller or reduced diameter implant section is first advanced within the intervertebral space followed by the larger implant section 64.

Figure 23:
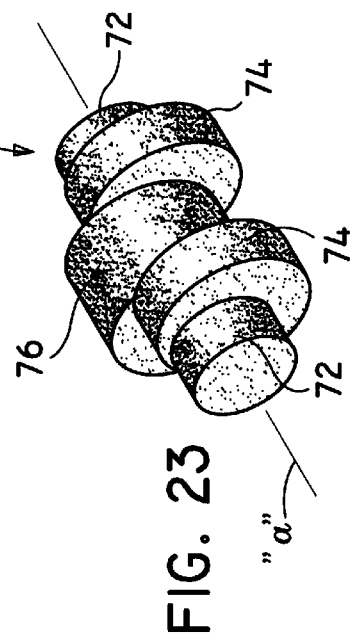

Implant sections 62,64 define retaining surface 66. FIG. 23 depicts another embodiment where the implant 70 has multi-steps with the implant sections 72,74,76 eccentrically arranged with relation to the axis "a" of the implant body.

Figure 24:
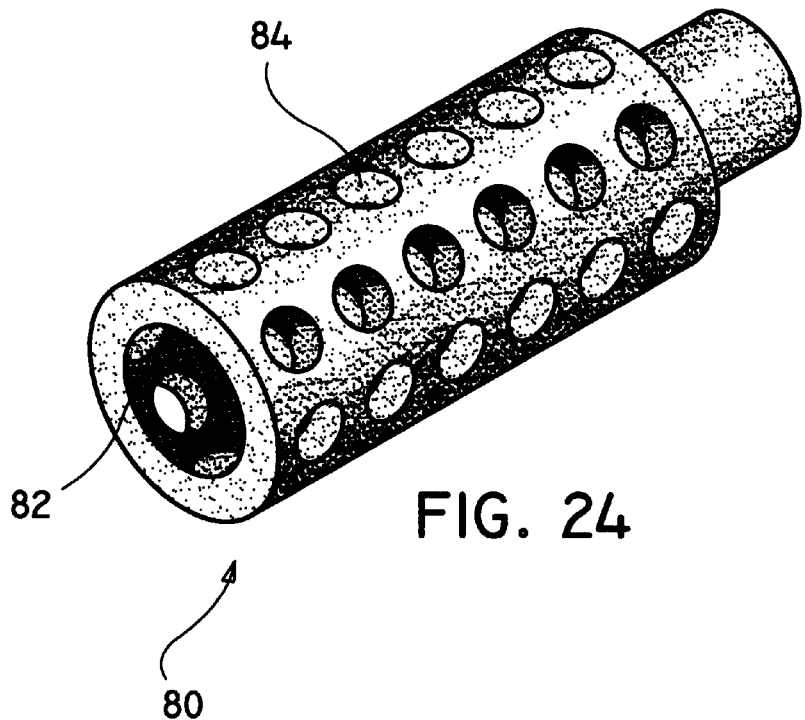
Figure 25:
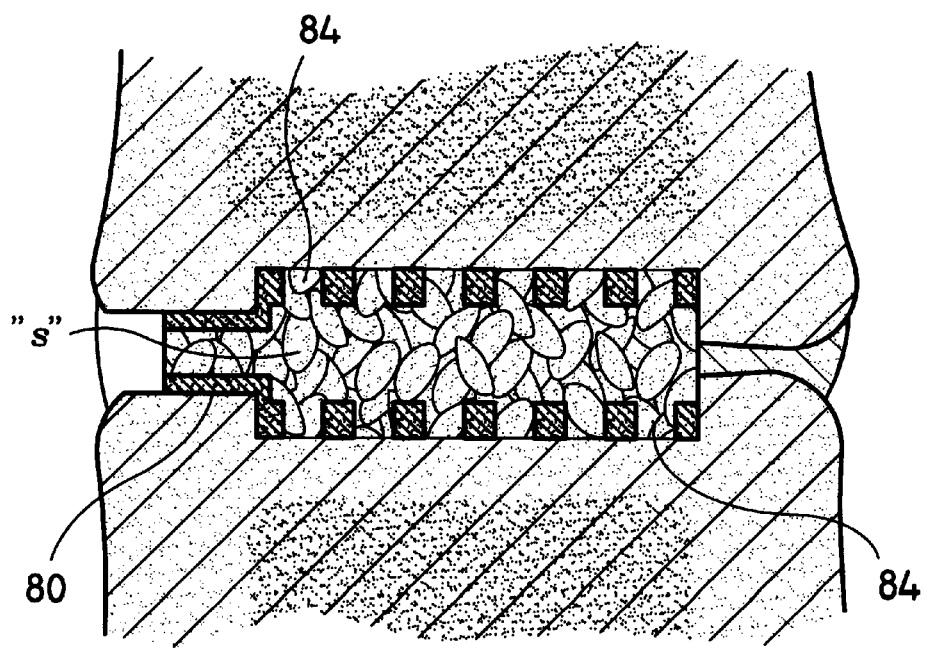

FIGS. 24–25 illustrate yet another embodiment of the fusion implant of the present invention. This implant 80 is similar to the implant of FIGS. 1–3, but, includes an internal bore or cavity 82 for accommodation of bone inducing substances "s" therein. The exterior wall of implant 80 includes a plurality of openings 84 which communicate with the internal bore 82. When inserted into the intervertebral space, the bone crosses over the outer surface of the cage into the internal cavity 82 and into contact with the bone inducing substances "s" therein. The bone inducing substances may be retrieved from the iliac crest as in conventional in the art. One form of bone inducing substances incorporable with the fusion implant of the present invention is disclosed in commonly assigned U.S. patent application Ser. No. 08/191,624, filed Feb. 4, 1994, the contents of which are incorporated herein by reference. The bone inducing substances disclosed in the '624 application include a flowable composition having a dimensionalized osteogenic bone powder in a flowable biocompatible carrier.

Figure 26:
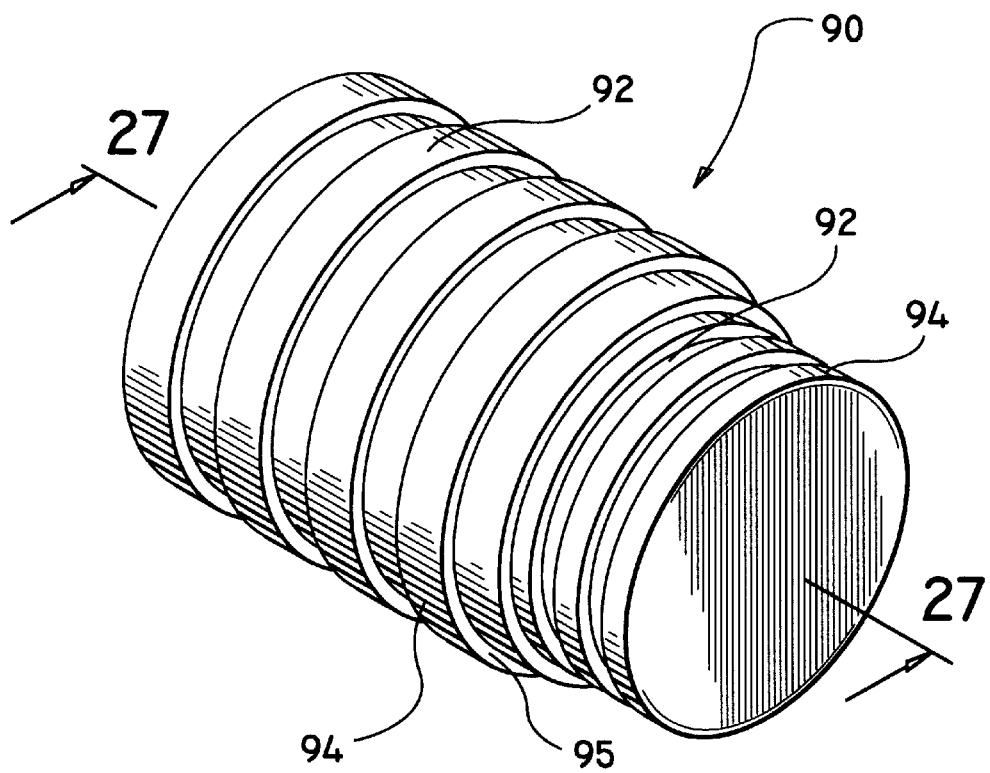
FIG. 26 is a perspective view of an alternate metallic dowel fusion implant.
Figure 27:
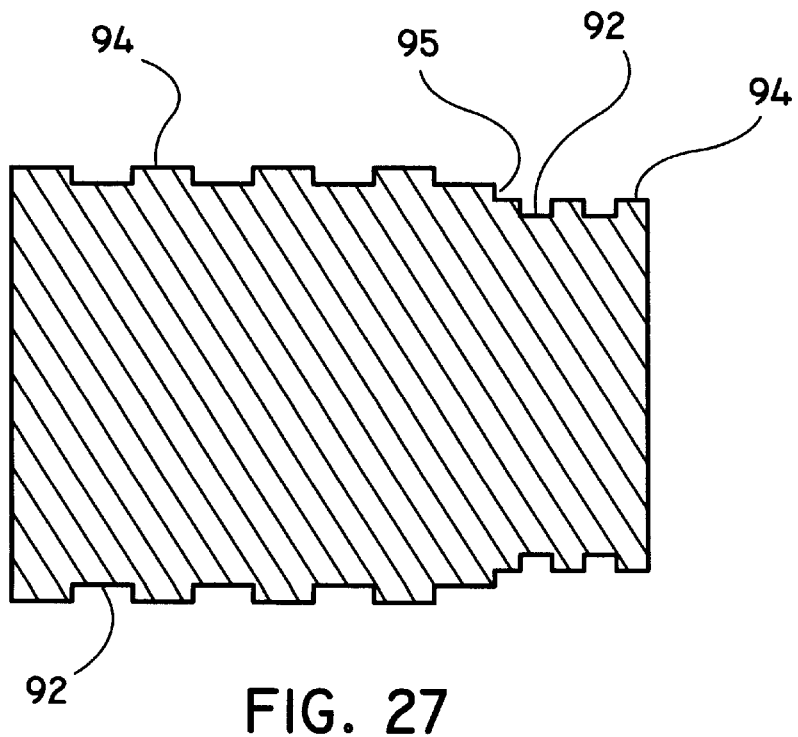
FIG. 27 is a cross-sectional view of the metallic dowel fusion implant taken along the lines 27—27 of FIG. 26.

Referring now to FIGS. 26–27, there is illustrated another embodiment of the present disclosure. Implant 90 is fabricated from a metallic material including titanium, its alloy, or surgical steel. Alternatively, implant 90 may be formed of ceramic or a suitable rigid polymeric material, or, in a further alternative, bone as described above. Implant 90 is similar in configuration to implant 10 of FIGS. 1–2, but, further includes a plurality of alternating annular grooves and ridges 92, 94 with stepped region 95. The grooves and ridges 92, 94 facilitate retention within the intervertebral space by increasing the surface area contact of the outer surface of the implant 90 with the vertebral bodies.

Figure 28:
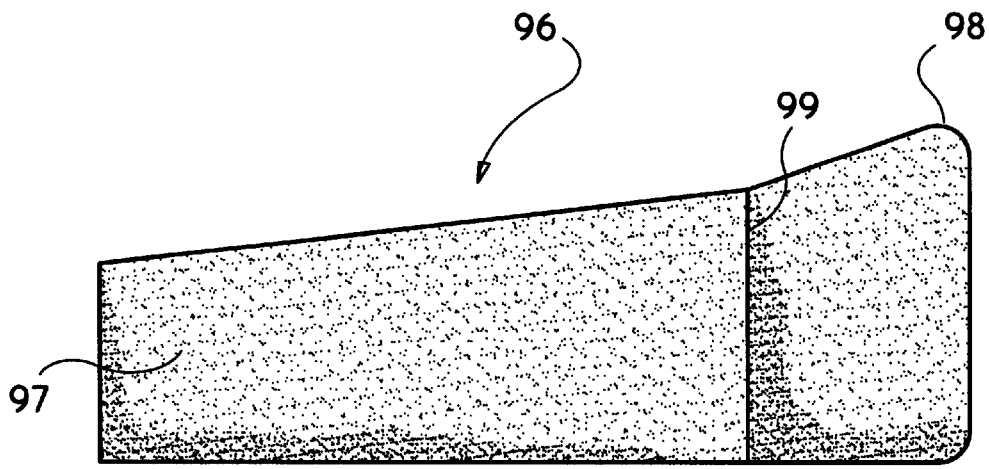
FIGS. 28–29 are side plan and top plan views of another alternate fusion implant having a wedge-shape configuration.
Figure 29:
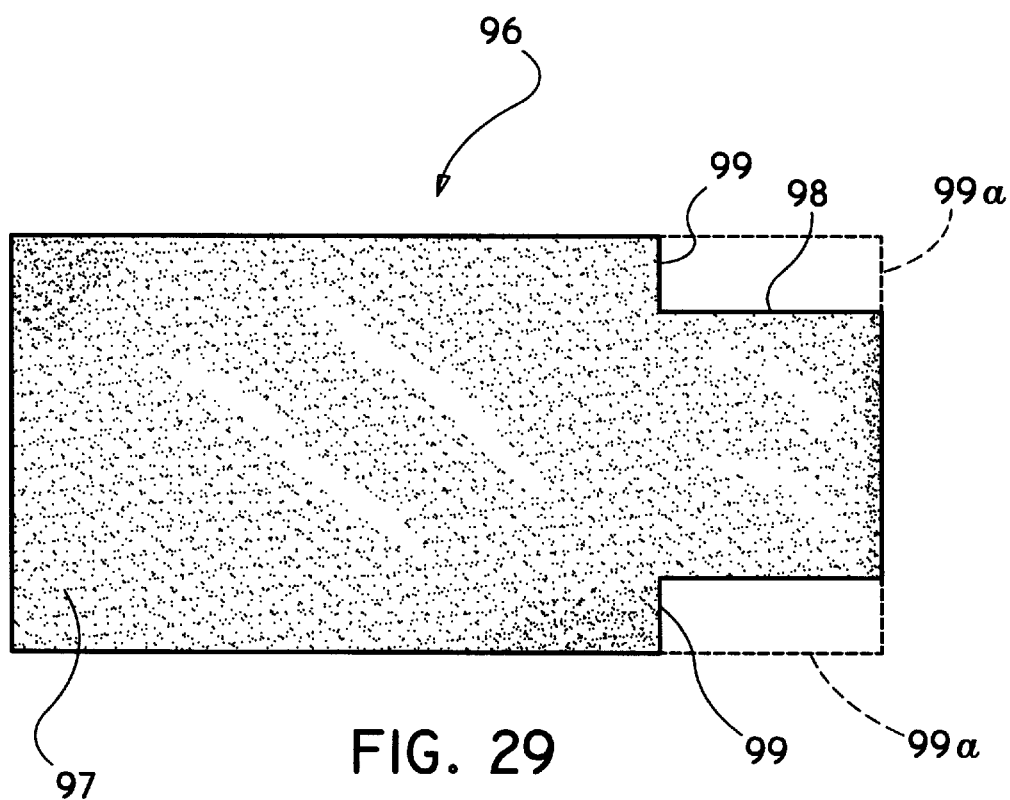
Figure 30:
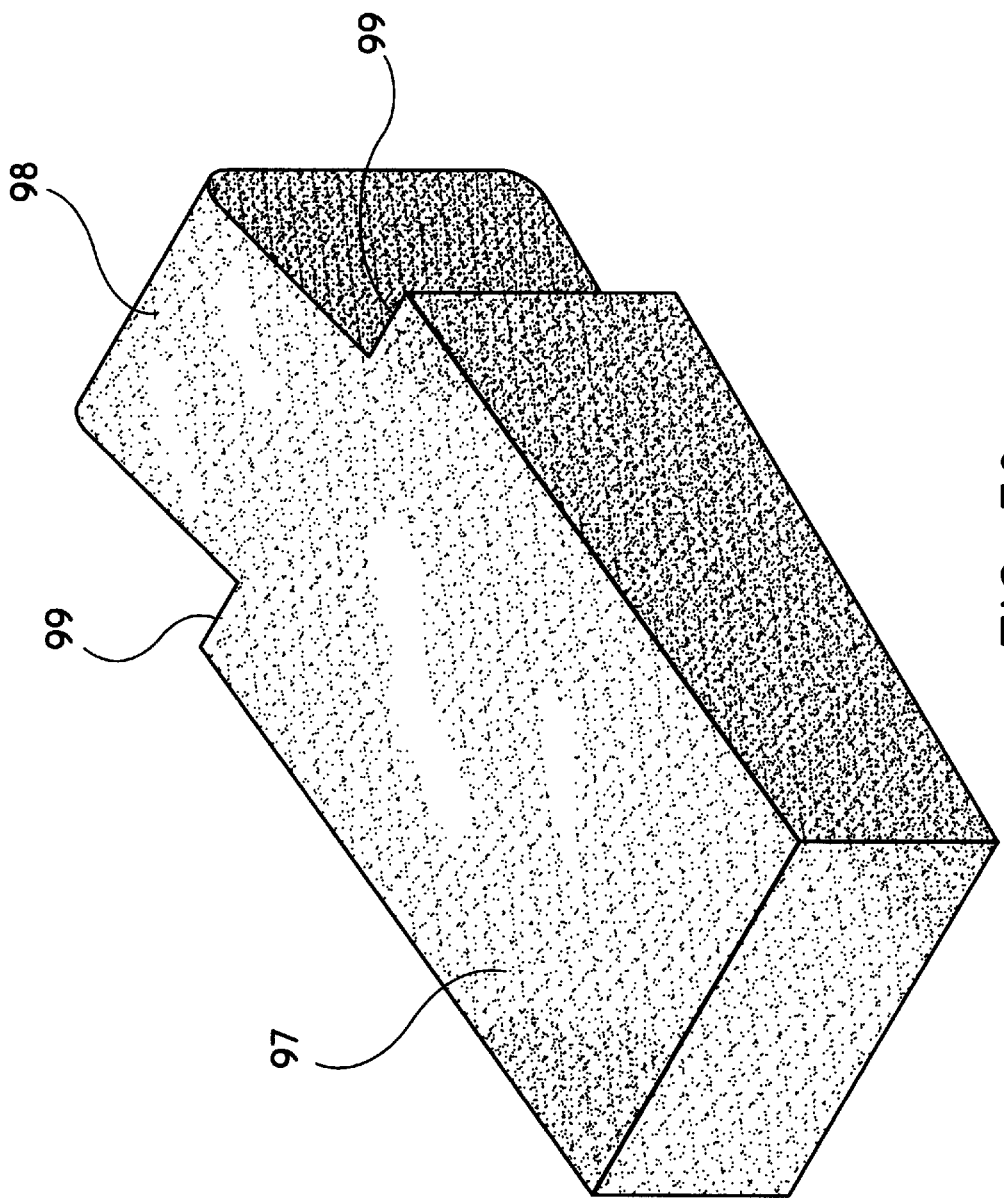
FIG. 30 is a perspective view of the fusion implant of FIGS. 28–29.

FIGS. 28–29 illustrate in side and plan views, respectively, another alternate embodiment of the fusion implant. FIG. 30 is a perspective view of the alternate embodiment. Implant 96 is generally wedge-shaped as shown and includes first and second sections 97, 98 and stepped regions 99 defined at the juncture of the longitudinal sections. The stepped regions 99 are preferably formed by removing opposed peripheral portions 99a (shown in phantom) of the second section 98. It is also envisioned that only one stepped region 99 can be formed instead of the two regions shown. Implant 96 is inserted within a correspondingly dimensioned bore defined in the adjacent vertebrae whereby stepped regions 99 engage vertebral surface defined by the preformed receiving bed in a manner similar to that described in connection with the embodiment of FIGS. 1–2.

It will be understood that various modifications can be made to the embodiments of the present invention herein disclosed without departing from the spirit thereof. The above description should not be construed as limiting the invention but merely as exemplifications of preferred embodiments thereof. Those skilled in the art will envision other modifications within the scope and spirit of the present invention as defined by the claims appended hereto.

What is claimed is:

1. An intervertebral prosthesis comprising an implant member having a first end and a second end and being dimensioned for insertion within a receiving bed formed in opposed faces of adjacent vertebrae, said implant member defining a longitudinal axis and having a first longitudinal section having a first planar surface and a second longitudinal section having a second planar surface, the implant member having a wedge-shaped configuration and a height which increases from the first end to the second end along the longitudinal axis, the first planar surface defining a first anile with respect to the longitudinal axis and the second planar surface defining a second angle with respect to the longitudinal axis, the second angle being greater than the first angle.

2. An intervertebral prosthesis according to claim 1, further including a retaining surface formed on the implant member, the retaining surface including at least one stepped region.

3. An intervertebral prosthesis according to claim 2, wherein the at least one stepped region includes two stepped regions.

4. An intervertebral prosthesis according to claim 2, wherein the at least one stepped region is formed by removing a portion of the second longitudinal section.

5. An intervertebral prosthesis according to claim 1, wherein the implant member is formed from bone.

6. An intervertebral prosthesis according to claim 5, wherein the bone comprises at least one of cancellous and cortical bone.

7. An intervertebral prosthesis according to claim 1, wherein the implant member comprises a biocompatible material selected from the group consisting of titanium, titanium alloys, surgical steel, polymeric material and ceramic material.

8. An intervertebral implant for insertion within a receiving bed located between adjacent vertebrae, the implant comprising a body having a longitudinal axis and including a front wall, a rear wall, a pair of sidewalls, a top surface and a bottom surface, the pair of sidewalls decreasing in height from the front wall to the rear wall such that the implant has a wedge-shaped configuration, and at least one cutout formed at the intersection of the front wall and at least one of the sidewalls and extending between the top and bottom surfaces, the cutout defining a stepped portion having one wall which is substantially parallel to the sidewalls and a second wall which is substantially parallel to the front and rear walls.

9. An intervertebral implant according to claim 8, wherein the at least one cutout includes first and second cutouts.

10. An intervertebral implant according to claim 8, wherein the implant is formed from bone.

11. An intervertebral implant according to claim 10, wherein the bone is selected from the group consisting of cancellous bone and cortical bone.

12. An intervertebral implant according to claim 8, wherein the implant comprises a biocompatible material selected from the group consisting of titanium, titanium alloys, surgical grade steel, polymeric material and ceramic material.

13. An intervertebral prosthesis according to claim 1, wherein the first end of the implant member defines the greatest height of the implant member.

\* \* \* \* \*